United States Patent [19]

Maximenko et al.

[11] 4,349,630
[45] Sep. 14, 1982

[54] HEAT-RESISTANT WATER SOLUBLE UROKINASE DERIVATIVE

[76] Inventors: Alexandr V. Maximenko, ulitsa Baltiiskaya, 10, korpus 3, kv. 144.; Vladimir P. Torchilin, Rostovskaya naberezhnaya, 1, kv. 90.; Vladimir N. Smirnov, Juzhinsky pereulok, 3, kv. 5.; Evgeny I. Chazov, Petroverigsky pereulok, 10., all of Moscow, U.S.S.R.

[21] Appl. No.: 183,093

[22] Filed: Aug. 27, 1980

[30] Foreign Application Priority Data

Sep. 28, 1979 [SU] U.S.S.R. .............................. 2821712

[51] Int. Cl.$^3$ .................... C12N 9/72; C12N 11/08; C12N 9/96
[52] U.S. Cl. .................................. 435/180; 435/215; 435/188

[58] Field of Search ............... 435/215, 178, 180, 181, 435/188

[56] References Cited

U.S. PATENT DOCUMENTS

| | | | |
|---|---|---|---|
| 3,625,827 | 12/1971 | Wildi et al. | 435/180 |
| 3,876,501 | 4/1975 | Hanushewsky | 435/178 |
| 4,106,992 | 8/1978 | Vairel et al. | 435/215 |

*Primary Examiner*—David M. Naff
*Assistant Examiner*—Kathleen McCowin
*Attorney, Agent, or Firm*—Steinberg & Raskin

[57] ABSTRACT

A heat-resistant water soluble derivative of urokinase is prepared which comprises urokinase covalently bonded to a copolymer of acrylamide and acrylic acid having a molecular weight of 10,000 to 200,000 and a content of acrylic acid of 1% to 2%. The derivative contains 15% to 35% urokinase and has an esterase and amidolytic activity of from 10% to 80%.

4 Claims, No Drawings

HEAT-RESISTANT WATER SOLUBLE UROKINASE DERIVATIVE

FIELD OF THE INVENTION

The present invention relates to the chemico-pharmaceutical industry and, more specifically, to novel compounds—heat-resistant urokinase derivatives and method for preparing same.

These novel compounds feature a thrombolytic activity and are useful in medicine as active principles of thrombolytic preparations, as well as in biology and biochemistry where the studies of thrombogenesis and functioning of enzymatic systems are carried out.

BACKGROUND OF THE INVENTION

The use of urokinase in medicine as an activator of plasminogen is well known, since it possesses well pronounced thrombolytic properties. Urokinase is employed in treatment of such diseases as pulmonary thromboembolism, thrombosis of deep veins, diseases of brain vessels and myocardial infarction. However the therapy by means of native urokinase is complicated due to its inactivation under the effect of blood inhibitors and endogenous proteases, as well as due to the impossibility of maintaining a high local content of the preparation in the injured organ. In the urokinase treatment, it is necessary to repeatedly administer high doses of the preparation. These difficulties can be surmounted through combining of the enzymes with high-molecular carriers. The enzyme derivatives possess an increased stability or resistance in respect of various inactivation factors; they also feature a delayed withdrawal from the organism.

Derivatives of urokinase combined with high-molecular carriers and methods for preparing the same are known. Thus, urokinase is combined with sepharose-4B (cf. Wiman B., Wallen P. Eur.J.Biochem., 35, 25, 1973) using activation of the carrier with cyanogen bromide. The use of such a highly toxic compound for medical purposes is impossible.

Also known is a method for preparing urokinase derivatives, wherein urokinase is "sewn-in" into the polyacrylamide gel (Capet. Antanini F. L., Tamenasse J., Can.J.Biochem., 53, 890, 1975) after treatment thereof with sodium nitrite in an acidic medium, the thus-diazotized carrier being reacted with the enzyme through azo-coupling. In this manner a water-insoluble urokinase derivative is obtained which, however, also cannot be employed in medicine.

Water-soluble heat-resistant urokinase derivatives possessing thrombolytic activity have not been hitherto described in the literature.

SUMMARY OF THE INVENTION

It is an object of the present invention to provide novel heat-resistant urokinase derivatives which are water-soluble and possess a long-action thrombolytic activity, and to provide a method for preparing these novel urokinase derivatives.

This object is accomplished by novel compounds which comprise derivatives of urokinase with a copolymer of acrylamide and acrylic acid with a molecular weight of from 10,000 to 200,000 conventional units and a content of acrylic acid of from 1 to 20% containing 15 to 35% of urokinase and having an esterase and amidolytic activity of from 10 to 80%.

The novel urokinase derivatives according to the present invention are in the form of a white powder which is readily soluble in water. These compounds feature an enhanced heat-resistance due to the formation of covalent bonds of enzyme-carrier; they also feature a long period of thrombolytic effect.

The method for preparing the novel heat-resistant urokinase derivatives according to the present invention comprises reacting a copolymer of acrylamide and acrylic acid, with a molecular weight of from 10,000 to 200,000 conventional units and the content of acrylic acid, of from 1 to 20%, with urokinase in the presence of an activator, i.e. 1-ethyl-3-(3-dimethylaminopropyl)carbodiimide at a temperature within a range of from 0° to 25° C. in a weakly-alkaline medium of a 0.001 to 1.0 M phosphate buffer, followed by isolation of the desired product. To obtain a high yield of the desired product, the reaction is carried out for 10 to 20 hours.

DETAILED DESCRIPTION OF THE INVENTION

The method for the addition of urokinase to the above-mentioned copolymer involves the stage of activation of carboxy groups of the copolymer with 1-ethyl-3-(3-dimethylaminopropyl)carbodiimide:

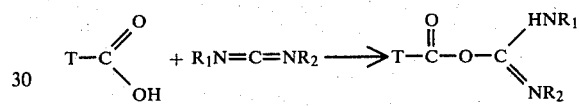

wherein T is a carrier, followed by reacting the activated carboxy groups of the carrier with the protein aminogroups:

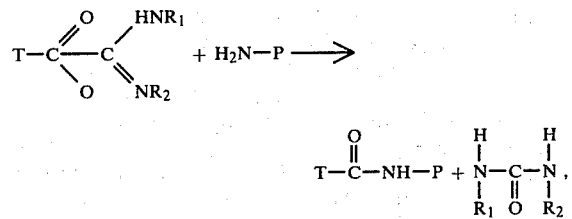

wherein P is enzyme.

The method according to the present invention is effected in the following manner.

A high-molecular carrier—a copolymer of acrylamide and acrylic acid with a molecular weight of from 10,000 to 200,000 conventional units and a content of acrylic acid of from 1 to 20% is dissolved at weakly alkaline pH values in a solution of a phosphate buffer (0.001 to 1.0 M), whereafter at a temperature of from 0° to 25° C. an activator, i.e. 1-ethyl-3-(3-dimethylaminopropyl)carbodiimide, is introduced into the solution and after some time a solution of urokinase in distilled water is added thereto. The combining reaction is preferably carried out for 10 to 20 hours, whereafter the resulting urokinase derivative is separated from other compounds by the method of gel-chromatography.

The thus-prepared product comprises urokinase chemically bonded with the synthetic polymeric carrier. The product retains totally its biological activity relative to the high-molecular substrates, does not lose its catalytic activity upon keeping in a cooler (4°–5° C.) in dissolved form for three months (in contrast to solutions of the native enzyme), and features an enhanced heat-resistance and prolonged thrombolytic activity.

The synthesis of the above-mentioned water-soluble polymeric carrier is effected by way of a radical copolymerization of the monomers in the presence of ammonium persulphate in an aqueous solution. The copolymerization is conducted at a temperature of 60° C. for 4 hours. The total concentration of the monomers in the reaction mixture is 5% by weight. The content of acrylic acid in the copolymer is equal to 1-20% by weight.

It should be noted that increasing the content of acrylic acid in the copolymer above 20% results in an increased amount of combined protein, while a low content (below 1%) of acrylic acid in the copolymer makes it biologically inert. The biocompatibility of this type carrier has been shown earlier wherefore they are employed as plasm substituents.

For a better understanding of the present invention some specific examples illustrating novel heat-resistant urokinase derivatives, the method of preparing the same and the tests of their thrombolytic activity are given hereinbelow.

EXAMPLE 1

In 4 ml of a 0.001 M phosphate buffer with the pH of 8.3 there are dissolved 20 mg of a copolymer of acrylamide and acrylic acid with a molecular weight of 100,000 conventional units and a content of acrylic acid of 3%. Then in the cold (4° C.) into this solution there are introduced 2.5 mg of 1-ethyl-3-(3-dimethylaminopropyl)-carbodiimide and after 20 minutes 1 ml of a solution of native urokinase in distilled water is added thereto, (250,000 ME/ml). The combining reaction is carried out for 16 hours, whereafter the resulting urokinase derivative is separated with the high-molecular carrier by means of gel-chromatography in a column with Sephadex G-150. The resulting product, as regards its kinetic parameters of hydrolysis of low-molecular substrates and heat-resistance, is not inferior to the native enzyme. Up to 80% of the starting amount of urokinase is combined with the carrier; the retained esterase and amidolytic activity is 78–81%. The resulting compound loses no catalytic activity relative to high-molecular substrates (plasmogen); in the in vitro system it lyses a simulated thromb just as the native urokinase preparation. Under physiological conditions at a temperature of 37° C. the resulting compound does not substantially lose its catalytic activity over two days. The native enzyme under the same conditions loses more than 50% of its catalytic activity.

EXAMPLE 2

The procedure of the foregoing Example 1 is repeated.

As the polymeric carrier use is made of a copolymer of acrylamide and acrylic acid with a molecular weight of 10,000 conventional units and a content of acrylic acid of 1%. The process is effected in a 0.1 M solution of phosphate buffer at a temperature of 25° C. for 20 hours. In this case the amount of the combined (with the carrier) urokinase is equal to 53% and the retained esterase and amidolytic activity of the preparation is equal to 50–51%.

EXAMPLE 3

The procedure is effected in a manner similar to that described in Example 1. Use is made of a copolymer of acrylamide and acrylic acid having a molecular weight of 200,000 conventional units and a content of acrylic acid of 20%. The reaction is conducted in a 1.0 M solution of a phosphate buffer at a temperature of 0° C. In this case 20% of urokinase of the starting total amount of the enzyme are combined with the carrier. The esterase and amidolytic activity retained by the preparation is 17%.

Therefore, urokinase derivatives prepared in Examples 1 to 3 contain different amounts of the enzyme combined with the carrier which is explained by the important role of the ionic strength value of the solution, depending on the phosphate buffer concentration in carrying out the combining reaction. All the urokinase derivatives possess thrombolytic activity comparative with that of the native urokinase. Furthermore, as is seen from Example 1, the thus-prepared compounds have an increased heat-resistance and retain their catalytic activity for a long time.

EXAMPLE 4

Testing of thrombolytic activity of the compounds produced in Examples 1 to 3 hereinabove was effected in comparison with the thrombolytic activity of the native urokinase preparation. Lysis of a thrombin clot is effected on the surface of a screen permeable for a homogeneous solution of protein and immersed into the solution so as to ensure washing of the artificial thromb surface with the uniformly agitated solution. The preparation of thrombs was carried out following a standard procedure by reaction of 0.5 ml of a solution of fibrinogen (10 mg/ml) with 0.2 ml of a solution of thrombion (4 mg/ml), whereafter the thromb is maintained for 4 hours. The thus-prepared thromb was immersed in a solution of a 0.1 M phosphate buffer with 0.02 M of bisodium salt of ethylenediamintetracetic acid with pH=7.4 so that its lower surface was washed with this solution; it contained a human plasminogen (Lys-Pmg 1,0 mg/ml). For thrombolysis the native urokinase and the resulting urokinase derivatives with the copolymers were taken in a ratio ensuring their identical esterase activity relative to the low-molecular substrate (AGlMe). The rate of lysis of the fibrin clot was observed by the variation (increase) of the solution optical density (due to destruction upon thrombolysis of the insoluble fibrin clot and passing of its fragments into solution) in a spectrophotometer at 280 nm with time.

The results of the thus-conducted experiments are shown in the following Table, wherein $tg\alpha$ is the ratio of optical density gain of the solution (as a result of destruction of the insoluble finrin clot upon thrombolysis and passing of its fragments into solution) to the period of time within which it took place. This is the parameter characterizing the thrombolysis rate.

TABLE

| Test Compound | Thromb lysis rate | |
|---|---|---|
| | $tg\alpha \dfrac{\Delta D \%_{280}}{\Delta t}$ | % |
| Native urokinase | 0.49 | 100 |
| Urokinase derivative of Example 1 | 0.61 | 125 |
| Urokinase derivative of Example 2 | 0.54 | 110 |
| Urokinase derivative of Example 3 | 0.51 | 104 |

Consequently, from the data shown in the above Table it is seen that the resulting urokinase derivatives with the copolymer are even superior of the native enzyme as to the effectiveness of its thrombolytic action. The increased heat-resistance of the resulting urokinase derivatives enables the enzyme to retain its catalytic activity for a longer period of time as compared to the native preparation which, in turn, results in prolongation of the thrombolytic effect of the thus-prepared urokinase derivatives.

What is claimed is:

1. A heat-resistant water soluble derivative of urokinase comprising urokinase covalently bonded to a copolymer of acrylamide and acrylic acid having a molecular weight of from 10,000 to 200,000 conventional units and a content of acrylic acid of from 1 to 20%, said derivative containing 15 to 35% of urokinase and having esterase and amidolytic activity of from 10 to 80%.

2. A method for preparing the heat-resistant water soluble urokinase derivative of claim 1, which comprises reacting a copolymer of acrylamide and acrylic acid having a molecular weight of from 10,000 to 200,000 conventional units and a content of acrylic acid of from 1 to 20% with urokinase in the presence of an activator at a temperature of from 0° to 25° C. in a weakly-alkaline medium of a 0.001 to 1.0 M phosphate buffer, and isolating the heat-resistant water soluble urokinase derivative.

3. The method of claim 2, wherein the reaction is conducted for a period of from 10 to 20 hours.

4. Method according to claim 2 wherein said activator is 1-ethyl-3-(3-dimethyl-aminopropyl) carbodiimide.

* * * * *